US00PP08259P

United States Patent [19]

Jacobsen

[11] Patent Number: Plant 8,259

[45] Date of Patent: Jun. 15, 1993

[54] POINSETTIA PLANT 'PETERSTAR'

[75] Inventor: Peter Jacobsen, Skibby, Denmark

[73] Assignee: Paul Ecke Ranch, Inc., Encinitas, Calif.

[21] Appl. No.: 727,641

[22] Filed: Jul. 10, 1991

[51] Int. Cl.[5] ..... A01H 5/00
[52] U.S. Cl. ..... Plt./86.4
[58] Field of Search ..... Plt./86.1–86.4

[56] References Cited

U.S. PATENT DOCUMENTS

P.P. 5,492 6/1985 Gutbier ..... Plt. 86.4

*Primary Examiner*—James R. Feyrer
*Attorney, Agent, or Firm*—Arnold, White & Durkee

[57] ABSTRACT

This new Poinsettia cultivar, designated 'Peterstar', is vigorous and self-branching, having a medium height and bright red flower bracts. 'Peterstar' originated as an induced mutation of 'Angelika' (U.S. Plant Pat. No. 5,492). 'Peterstar' is shorter and blooms earlier than 'Angelika', the cultivar it most closely resembles. The bracts are wider and smoother than those of 'Angelika'.

1 Drawing Sheet

BACKGROUND OF THE INVENTION

'Peterstar' is a vigorous, strong growing Poinsettia of medium height and large, bright red flower bracts. It has self-branching traits which make it desirable for branched plant production. 'Peterstar' blooms relatively early and the blooming time is very uniform among individual clones. The bract presentation is slightly umbrella shaped, but the plant does not exhibit epinasty after sleeving and shipping.

This new Poinsettia cultivar originated in a greenhouse in Skibby, Denmark as an induced mutation of the red bracted cultivar 'Angelika' (U.S. Plant Pat. No. 5,492). The Poinsettia of the present invention was induced from the variety 'Angelika' using 2500 RAD of gamma rays, and was selected from about 200 mutants so produced. It most closely resembles the cultivar 'Angelika' but distinctly differs in the following traits. 'Peterstar' has a more compact growth habit than 'Angelika'. No growth (retarding) hormone is needed to obtain the compact stature of 'Peterstar'. In contrast, to get this same compactness with 'Angelika', you have to treat this variety with a rather high dosage of Cycocel. 'Peterstar' has wider bracts and the bract surface is relatively smoother than 'Angelika'. The bright red color of 'Peterstar' is uniform across the entire bract surface, whereas the red bracts of 'Angelika' fade along the margins. 'Peterstar' blooms 3–4 days earlier than 'Angelika'. This mutant was selected because of its distinctive characteristics which seem to make it commercially more desirable than the parent plant 'Angelika'.

After selection, vegetative reproduction of this plant was accomplished by stem cuttings for further testing purposes. Clones were subjected to successive generations of vegetative propagation which demonstrated that bract coloration, smooth bracts, early flowering and other distinctive characteristics held true from generation to generation.

DESCRIPTION OF THE PHOTOGRAPHS

Poinsettia cultivar 'Peterstar' is illustrated in the accompanying color photographs.

The upper photo is a side view of a typical pinched plant with several flowering stems.

The lower photo is a top view of the same plant showing flower and bract formation.

DESCRIPTION OF THE PLANT

The following is a detailed description of this new Poinsettia as observed in greenhouses in Encinitas, Calif., during December, 1990. Some observations are compared to the cultivar 'Angelika', U.S. Plant Pat. No. 5,492, grown at the same time, in the same greenhouse and under the same cultural conditions. Color designations are compared to the 1986 edition of R.H.S. Colour Chart, first published in 1966 by the Royal Horticultural Society, London, England.

THE PLANT

Origin: An induced mutation of 'Angelika' (U.S. Plant Pat. No. 5,492).

Classification:

*Botanic.*—*Euphorbia pulcherrima* Willd.
*Common name.*—Poinsettia.
*Cultivar name.*—'Peterstar'.

Form: Shrub.

Height: Medium.

Growth habit: As a single stemmed plant, upright and vigorous. In full flower, the stem is terminated by a large inflorescence, with smaller flowering side shoots lower on the stem. The average overall height of single stemmed plants was 43 cm. for 'Peterstar' compared to 48 cm. height for 'Angelika'.

Branching: Branching can be enhanced by removal of the stem tip. Then, several flowering branches with equal vigor will develop on a single plant.

Growth rate: Very fast. Rooting of stem cuttings occurs in 12–18 days under intermittent mist. The plant will flower in about nine weeks under continuous long night conditions and night temperatures of about 16–18 degrees C. Flowering is 3–4 days earlier than 'Angelika'.

Foliage: The foliage is clean and uniformly dark green from bottom to top of the plant. The leaves are of medium size, leaf blades typically being 13–15 cm.

long and 9-10 cm. wide with leaf petioles 5-6 cm. long.

*Leaf shape.*—Typical leaves are ovate with obtuse bases and acuminate tips. Leaf margins are mostly entire. An occasional leaf is modestly lobed with one small lobe on either side of the leaf blade.

*Leaf surface.*—Upper surface is glabrous and smooth. The under surface is slightly pubescent.

*Color.*—Upper side — Darker than RHS 147A. Under side — Near RHS 147B.

*Retention.*—The foliage retention is good even under low light intensities in the consumer's home.

Bracts: Generally there are 21-24 bracts of various sizes subtending the cyathia, as compared to the parent 'Angelika', which typically exhibits about 17 to 12 bracts in overlapping arrangement with a tight center. The primary bracts have blades typically 16-18 cm. long and 11-13 cm. wide with petioles 2-3 cm. long.

*Shape.*—Bracts are mostly ovate to elliptic on smaller bracts, with acute bases and acuminate tips. Bract margins are mostly entire, but primary bracts may have slight lobing on either side of the bracts.

*Surface.*—The bract surface is only slightly rugose and smoother than the bract surface of 'Angelika'.

*Color.*—Upper side — Bright red, near RHS 46B. The color of the bracts is uniform compared to 'Angelika', whose bract color fades near the margins. Under side — Red, near RHS 45C.

Cyathia: Generally, 18-21 cyathia (flowers) develop when the plant is in "full bloom". Each cyathium is 6-7 mm long and 5-6 mm wide, green in color, and fringed with red at the distal end. Either one or two yellow nectar cups protrude from the side of each cyathium. The flower pedicel is green and 5-6 mm in length. The stamens protruding from the cyathia are dark red. No viable seeds are formed. 'Peterstar' has abortive anthers (no pollen), is male sterile and probably also female sterile, as seeds set after crossing with this variety have never been seen. There are typically 10-12 anthers ripening at any one time. The pollen produced is yellow and copious.

Retention: The post production retention of the cyathia is good.

What is claimed is:

1. A new and distinct Poinsettia cultivar, substantially as herein shown and described, distinguished by its vigorous and self-branching growth habits, medium height and bright red flower bracts.

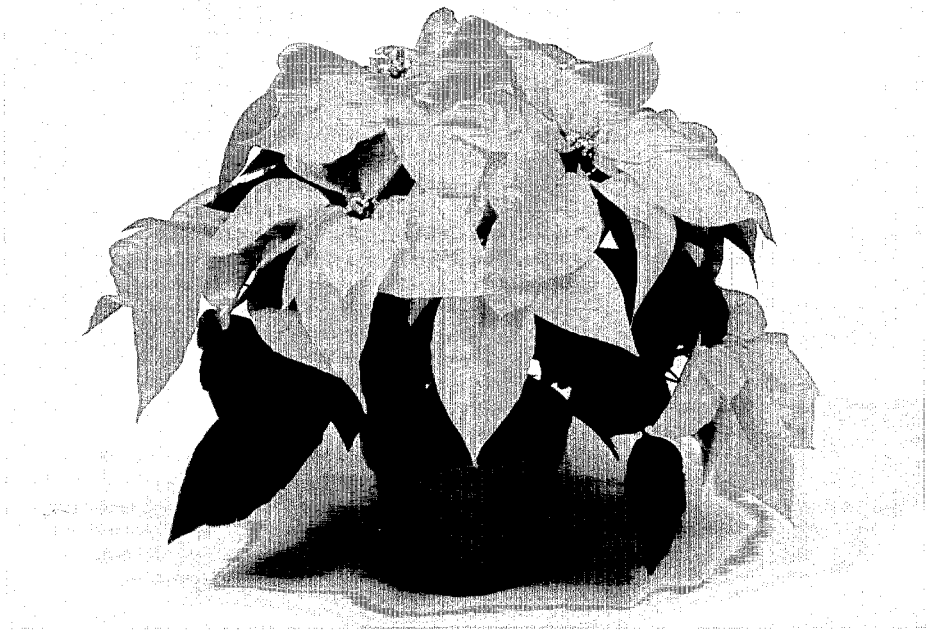
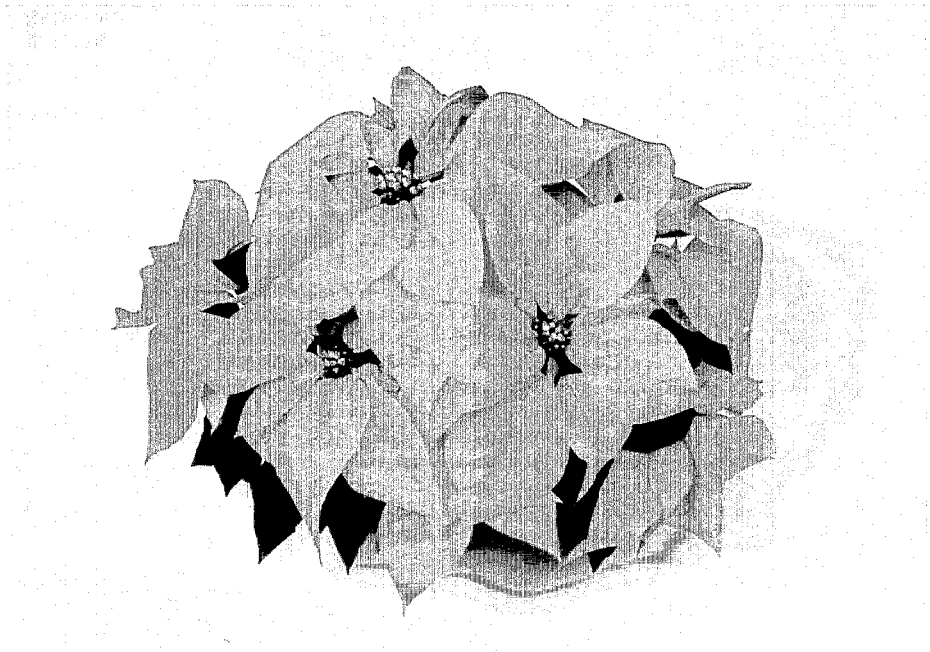

* * * * *